(12) United States Patent
Krall et al.

(10) Patent No.: US 9,237,843 B1
(45) Date of Patent: Jan. 19, 2016

(54) SYSTEM FOR MEASURING VISUAL FIXATION DISPARITY

(71) Applicant: eyeBrain Medical, Inc., San Diego, CA (US)

(72) Inventors: Jeffrey P. Krall, Mitchell, SD (US); Vance Thompson, Sioux Falls, SD (US); John Merril Davis, III, Midlothian, VA (US)

(73) Assignee: eyeBrain Medical, Inc., San Diego, CA (US)

( * ) Notice: Subject to any disclaimer, the term of this patent is extended or adjusted under 35 U.S.C. 154(b) by 7 days.

(21) Appl. No.: 14/324,629

(22) Filed: Jul. 7, 2014

(51) Int. Cl.
*A61B 3/02* (2006.01)
*A61B 3/14* (2006.01)
*A61B 3/08* (2006.01)
*G06F 3/01* (2006.01)
*A61B 3/113* (2006.01)

(52) U.S. Cl.
CPC . *A61B 3/08* (2013.01); *A61B 3/113* (2013.01); *G06F 3/013* (2013.01)

(58) Field of Classification Search
CPC .......... A61B 3/113; A61B 3/08; G06F 3/013
USPC .................................................. 351/209, 240
See application file for complete search history.

(56) References Cited

U.S. PATENT DOCUMENTS 5,026,151 A 6/1991 Waltuck
2013/0308099 A1 11/2013 Stack

*Primary Examiner* — William Choi
(74) *Attorney, Agent, or Firm* — Wood, Phillips, Katz, Clark & Mortimer

(57) ABSTRACT

There is disclosed herein a system for measuring visual fixation disparity comprising a display apparatus for presenting stereoscopic visual content to a patient. A sensing apparatus tracks eye movement of the patient. A controller controls the display apparatus to stereoscopically display a central image target alternately to a left eye and a right eye of the patient and tracking eye movement for a period of time as the central image target is alternated between the left eye and the right eye, and incrementally relocating the central image target left and right images until the patient perceives the left and right images to be physically coincident.

22 Claims, 13 Drawing Sheets

SYSTEM FOR MEASURING VISUAL FIXATION DISPARITY

CROSS-REFERENCE TO RELATED APPLICATIONS

Not Applicable.

FEDERALLY SPONSORED RESEARCH OR DEVELOPMENT

Not Applicable.

MICROFICHE/COPYRIGHT REFERENCE

Not Applicable.

FIELD

This application relates to vision correction and, more particularly, to measuring fixation disparity of the visual system.

BACKGROUND

The optical system of the human eye uses numerous muscles as well as central and peripheral cues while focusing on targets both near and far. There are many responses involved in changing focus from distant to near as well as fixating on a target at a set distance.

When our eyes are working together and are directed at a target greater than twenty feet from our eyes they will appear to be parallel with each other and we deem this binocularity. If both eyes are looking at a target closer than twenty feet our eyes may not look parallel but we a still have binocular vision as long as the line of sight of each eye is pointing directly at the target of regard. If binocularity is canceled by interrupting the vision of one eye or the other the eyes often rotate along X, Y, & Z-axis. The movement and rotation of the eye that is covered compared to the movement of the eye that is uncovered may be different, but measurable. In general terms the change in position or movement of the eyes once vision is interrupted, ending binocularity, is often deemed a heterophoria. It is also possible to measure the torsional rotation and movement along the X, Y, & Z axis of the eye by not interrupting one eye or disrupting binocularity. This may be done by altering the position of peripheral binocular targets located in a relationship to the central binocular targets.

Our proprioceptive system, or what we often call our "sixth sense", is the sensory feedback mechanism for motor control and posture. It gives us unconscious feedback internally. Our proprioceptive system is composed of sensory neurons located in our inner ear and stretch receptors located in our muscles and supporting ligaments.

In our skeletal muscles these proprioceptive receptors have a load compensating mechanism. For example: imagine standing with eyes closed and arms extended outward. Now imagine someone starting to load one book after another on your hands. As you feel the weight of the books increase, you exert more force in order to keep the books from falling to the ground. When maximum effort is reached the books will fall from your hands. You do not need your eyes to sense the weight.

There are anatomically similar proprioceptive receptors in our ocular muscles but these receptors do not have a load compensating mechanism and do not mediate conscious eye position. This is understandable because there is a constant mechanical load on all the extraocular muscles and no load compensating mechanism is required.

Our extraocular muscles have proprioceptive receptors that constantly give feedback to the location of each eye. When we choose to look at something our brain takes the image from each eye and moves our extraocular muscles to exactly line up to the target. If this did not happen you would have blurred vision one eye pointing at one target and the other eye pointing at a different target.

You can choose where you want to look but then your autonomic nervous system takes the image from each eye and sends a signal to your extraocular muscles to line each eye up perfectly at that target. After the movement of each eye independently to line up the target the proprioceptive receptors in your extraocular muscles send the signal back to brain as to the position of where each eyes has been moved to. This proprioceptive feedback is necessary to close the loop between where the brain told the eyes to move and where the eyes are currently located. The brain needs to know the position of each eye so that when you decide to look at the next target your brain knows how much to move each eye in order to line up to the next target.

This proprioceptive feedback is critical for coordinating the movements between our eyes, seeing a single clear image, along with many other functions. We know that this proprioceptive feedback from our extraocular muscles sends its signal via the trigeminal nerve, which is a nerve in our head responsible for pain sensation in our sinuses, extraocular muscle tissue, and jaw.

Many people who suffer from chronic headaches, asthenopia associated with near work, asthenopia associated with viewing distance targets, stiff neck and shoulder muscles, and dry eyes are the consequence of the extra ocular muscles proprioceptive sensory feedback mechanism stimulating the trigeminal nerve. From clinical study with chronic headache patients we have learned that changing this feedback loop can alter and often alleviate headache pain. This can be done by measuring proprioceptive disparity or more generally visual fixation disparity. Proprioceptive disparity is the imbalance between where the eyes are consciously focused and the nonvisual perception of where the object is located in space. This often varies with distance.

Testing and synchronizing the proprioceptive feedback between each extraocular muscle requires isolating our central vision from our peripheral vision. Our central vision sustains less than 1° of arc and is responsible for detailed vision located within the area of our retina called our fovea. Targets seen in the fovea are controlled by slow smooth pursuits eye movements. Targets outside of our fovea and in our peripheral vision are controlled by quick saccadic eye movements. Anatomically we know that pursuits and saccadic eye movements are coordinated in our brain from different locations.

The use of electronic image capture devices to observe and quantify the movement of the human eye is a mature technology known as "eye tracking". Some applications of eye tracking include military equipment for pilots, sophisticated 3-D virtual reality environments, and medical analysis.

Good quality stereo 3-D display technology is relatively new to consumer products, but has been available for professional applications for many years. A variety of 3-D display technologies have been developed which endeavor to provide the viewer with two visual images, one for each eye, which differ slightly in their content so as to present all targets in the visual field with their mathematically correct parallax according to distance from the viewer. The oldest movie technology used different glasses with colored filters for each eye. This was crude and unrealistic. Current technology for movies uses glasses with either passive polarized filters or active-shutter electronics. New technologies for single user displays are autostereoscopic (i.e., not requiring glasses) and incorporate lenticular lenses or parallax barriers to provide separate images for each eye.

This application is directed to improvements in testing proprioceptive feedback.

SUMMARY

This application relates to a system for measuring visual fixation disparity which uses a stereoscopic display in conjunction with eye tracking.

There is disclosed in accordance with one aspect a system for measuring visual fixation disparity comprising a display apparatus for presenting stereoscopic visual content to a patient. A sensing apparatus monitors central vision of the patient. A controller controls the display apparatus to stereoscopically display a smoothly moving peripheral target with a static central image target to isolate central vision from peripheral vision of the patient and monitor the central vision of the patient.

It is a feature that the display apparatus comprises a stereo LCD display and synchronously driven LCD shutters.

It is another feature that the display apparatus comprises a polarized light stereo display and matching polarized eye filters.

It is a further feature that the sensing apparatus comprises left and right image capture devices for tracking pupil position of the patient's left and right eyes, respectively. The sensing apparatus may be selectively adjustable to space the left and right image capture devices corresponding to the patient's pupillary distance.

It is still another feature that the controller controls the display apparatus to stereoscopically display a central image target alternately to a left eye and a right eye of the patient and tracking eye movement for a period of time as the central image target is alternated between the left eye and the right eye, and incrementally relocating the central image target left and right images until the patient perceives the left and right images to be physically coincident.

It is still another feature that the peripheral target and the central image target are stereoscopically consistent with each other.

It is yet a further feature that the peripheral target and the central image target are intentionally stereoscopically inconsistent with each other.

It is still a further feature that the controller controls the display apparatus to stereoscopically display a plurality of smoothly moving peripheral targets with the static central image target.

There is also disclosed herein a system for measuring visual fixation disparity comprising a display apparatus for presenting stereoscopic visual content to a patient. A sensing apparatus tracks eye movement of the patient. A controller controls the display apparatus to stereoscopically display a central image target alternately to a left eye and a right eye of the patient and tracking eye movement for a period of time as the central image target is alternated between the left eye and the right eye, and incrementally relocating the central image target left and right images until the patient perceives the left and right images to be physically coincident.

In one aspect the controller controls the display apparatus to stereoscopically display a peripheral target stereoscopically consistent with the static central image target to isolate central vision from peripheral vision of the patient and monitor the central vision of the patient.

In accordance with another aspect, the controller controls the display apparatus to stereoscopically display a moving peripheral target stereoscopically consistent with the static central image target to isolate central vision from peripheral vision of the patient and monitor the central vision of the patient.

In yet another aspect, the controller controls the display apparatus to stereoscopically display a peripheral target intentionally stereoscopically inconsistent with the static central image target to isolate central vision from peripheral vision of the patient and monitor the central vision of the patient.

In yet another aspect, the controller controls the display apparatus to stereoscopically display a moving peripheral target intentionally stereoscopically inconsistent with the static central image target to isolate central vision from peripheral vision of the patient and monitor the central vision of the patient.

It is a feature that the controller determines eye movement for each eye between a time that the central image target is not visible to each eye and a time that the central image target is visible to each eye. The controller may relocate the central image target until eye movement is less than a select amount, or until there is substantially no eye movement.

Other features and advantages will be apparent from a review of the entire specification, including the appended claims and drawings.

DETAILED DESCRIPTION

Figure 1:
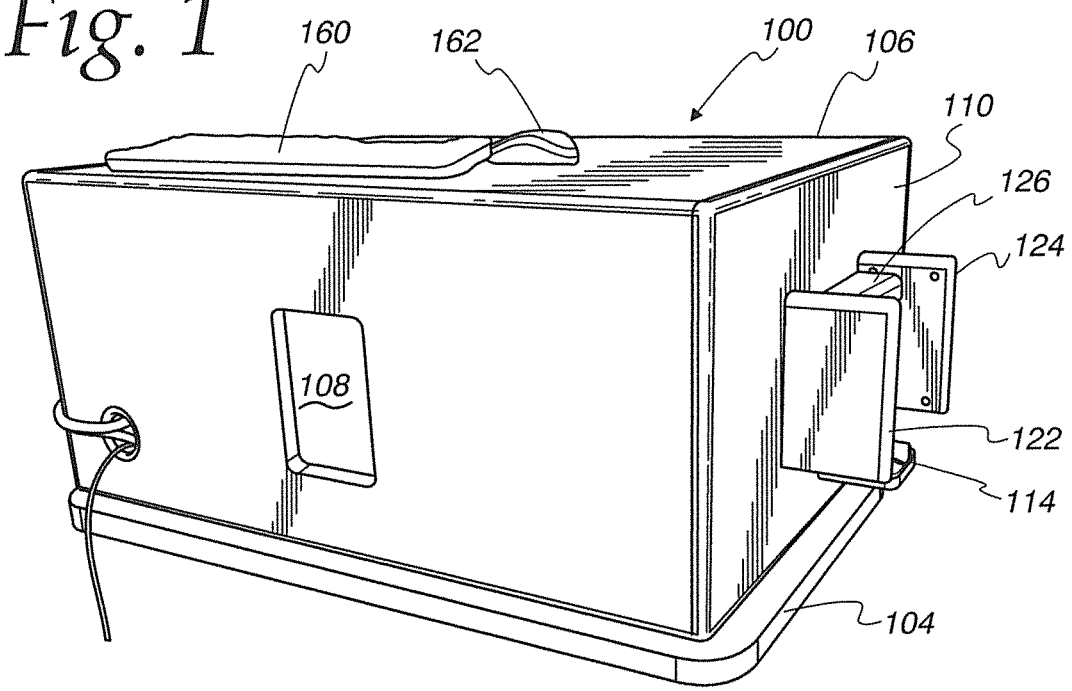
FIG. 1 is a perspective view of a system for measuring visual fixation disparity.

The measurement of visual fixation disparity, including proprioceptive disparity, for diagnosis and subsequent refractive lens treatment requires that the fixation disparity be measured with a repeatable accuracy that is independent both of the patient's subjective feedback and of the administering medical practitioner's technique. Problems exist with prior methods and systems for accomplishing appropriate measurement due to both of these factors.

The systems and methodology described herein allow medical professionals to accurately measure patient visual fixation disparity. To this end, the measurements are made in a fully automated process which requires the patient's cooperation, not the patient's interpretation of the visual presentation. The combination of the system and its automated functionality provides unique solutions to this problem.

The system described herein presents stereoscopic visual content to the patient. Continuous eye movement is a characteristic of human vision. The brain must necessarily quickly correlate fragments of moving images from both eyes to achieve a 3-D mental model of the body and its position in movement relative to its surroundings. At the same time, the patient's central vision must be able to employ its superior acuity to recognize targets and determine their position relative to the body. Catching a ball while running is an extreme example of this human ability. The achievement of neurological stereoscopic fusion in the brain of the patient simultaneously of both peripheral and central images is necessary as one part of the measurement process. In accordance with one aspect, the system disclosed herein uses a synthesized stereoscopic 3-D image incorporating a smoothly moving peripheral image target combined with a static but central image target that forms an effective visually compelling methodology to accomplish this aspect.

In accordance with another aspect, eye tracking is used in the context of the stereoscopic display of central and peripheral images. In a portion of the measurement process, the peripheral image is maintained while the left and right eye images of the central vision target are precisely displaced from their mathematically correct positions by an amount which may be expressed in optical diopters of prism. The central image is "flashed" to help "break" the fusion in the patient's brain and the patient's eyes are closely watched for movement by image capture devices. The presence of eye movement correlating with the appearance of the central image target indicates when the patient perceives two distinct targets rather than one. This allows for interpreting the patient's degree of fusion of the central vision target in the context of conflicting information from the patient's fusion of the moving peripheral target.

A system is disclosed herein which implements the two novel aspects described above. An illustrative hardware platform used to implement the visual content consists of standard 3-D stereo display technology in the form of a stereo-capable projector or display monitor and video electronics capable of supporting a pair of active-shutter glasses or a polarized light stereo display and matching polarized eye filters. Without loss of generality, the platform could also be equipment capable of autostereoscopy such as those which incorporate lenticular lenses or a parallax barrier, or combinations of two displays with half mirrors. A standard computer with a 3-D stereo-capable video graphics card and display monitor or projector, which are well known in the art, use conventional software applications to create the simple stereo display images. The software applications could be, for example, OpenGL or DirectX® (a registered trademark of Microsoft Corporation). The eye tracking function can be implemented with a pair of image capture devices and conventional professional grade image capture video hardware and image correlating software. Although other implementations may be desirable, the particular implementation of the hardware disclosed herein is not required for the invention as defined by the claims herein.

Figure 4:
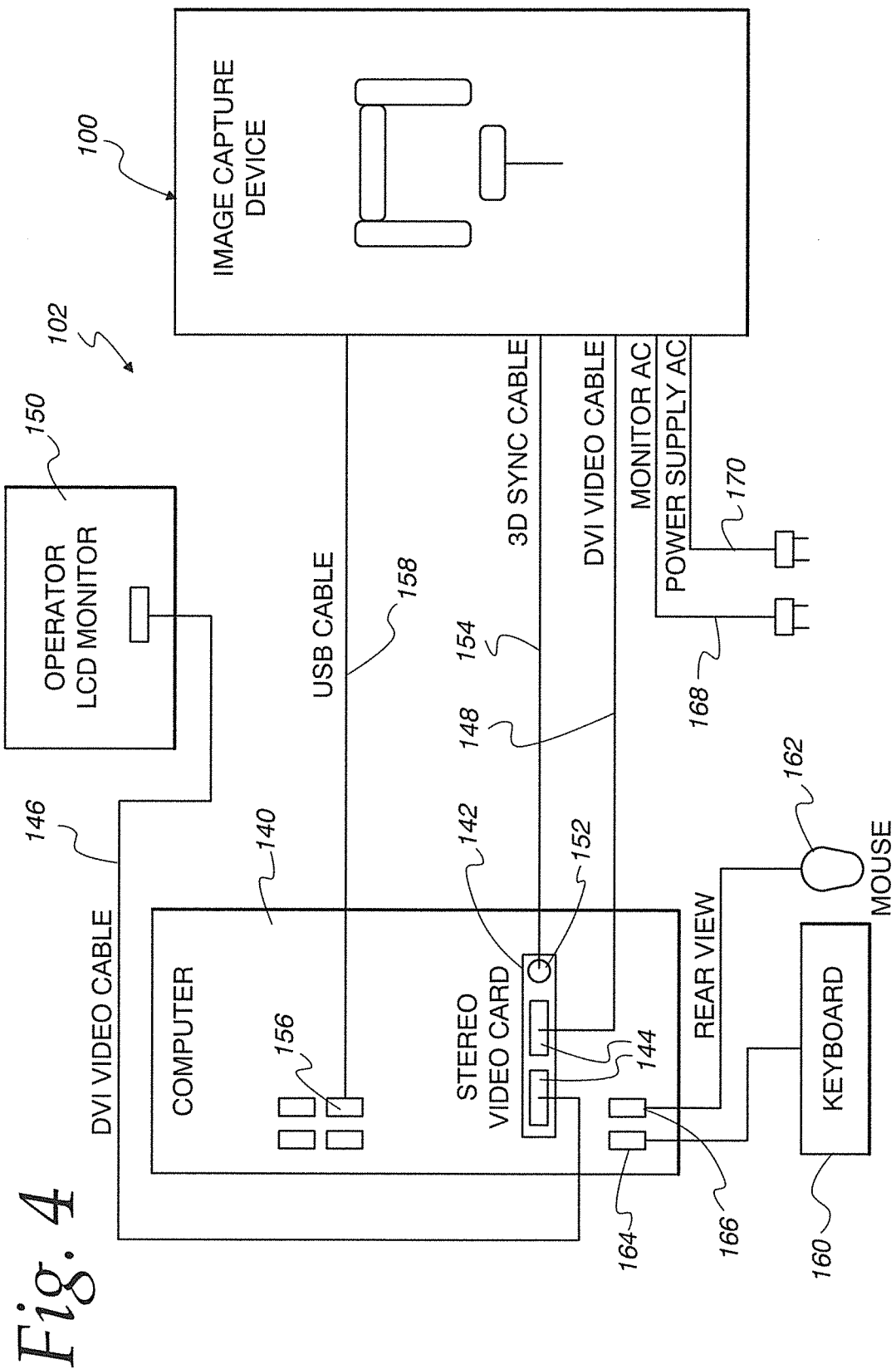
FIG. 4 is a block diagram for the system of FIG. 1.

Referring initially to FIG. 1, an image capture device 100 is illustrated forming part of a system 102 for measuring visual fixation disparity, see FIG. 4. The image capture device 100 comprises a housing base 104 and housing cover 106 to define an interior space 108. In the illustrated embodiment, the base 104 and cover 106 define a parallelepiped shaped housing, although the particular shape is not critical.

Figure 2:
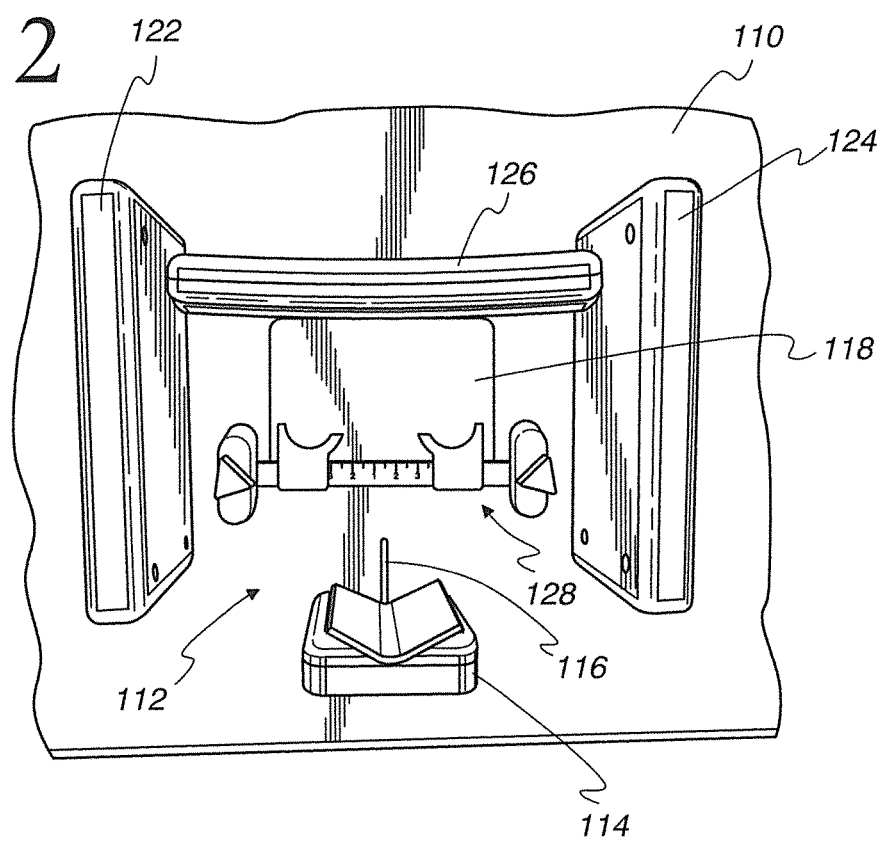
FIG. 2 is a partial front elevation view of the system of FIG. 1.

The cover 106 includes a front wall 110, see also FIG. 2, including a patient positioning apparatus 112. The positioning apparatus 112 comprises a chin support 114 which is selectively movable up and down via a front wall slot 116 to appropriately position the patient's eyes relative to a translucent black acrylic lens 118 covering a front opening 120, see FIG. 3. Generally rectangular side shields 122 and 124 extend outwardly from the front wall 110 on either side of the opening 120. A forehead rest 126 extends outwardly from the front wall 110 between the side plates 122 and 124. The shields 122 and 124 and the forehead rest 126 prevent ambient light from interfering with the operation. A conventional lens holder 128 is optionally mounted to the front wall 110 using apertures 130, see FIG. 3, for holding ophthalmic lenses equivalent to a patient's eyeglass prescription.

Figure 3:
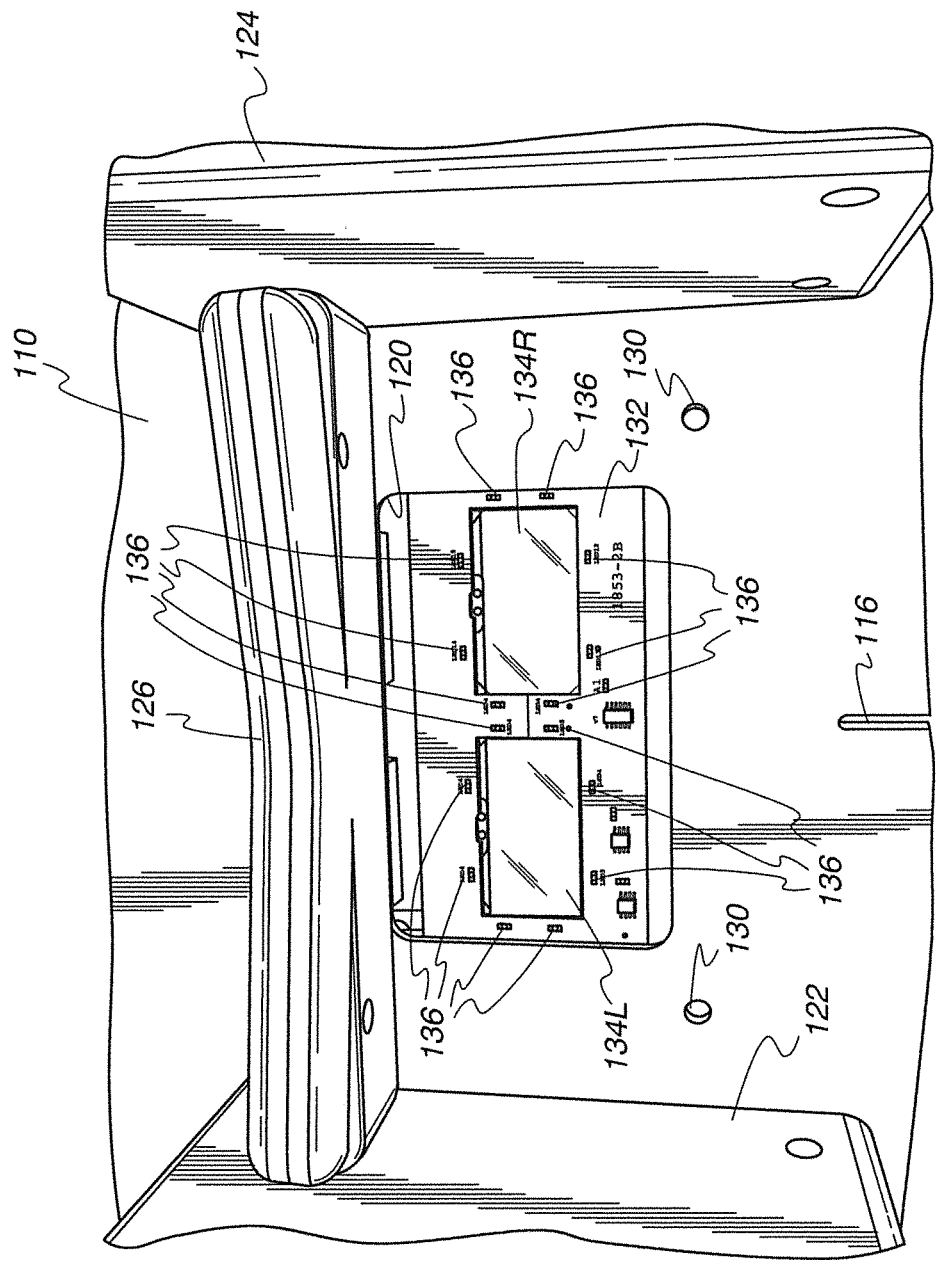
FIG. 3 is a view similar to FIG. 2 with an acrylic lens removed.

Referring to FIG. 3, the front wall 110 is illustrated with the acrylic lens 118, see FIG. 2, removed to show a printed circuit board 132 mounted across the opening 120. The printed circuit board 132 includes a left LCD shutter 134L and a right LCD shutter 134R. Each of the shutters 134L and 134R is surrounded by eight infrared LEDs 136. As described below, the user's chin is rested on the chin support 114 which is then raised or lowered to appropriately position the patient so that the patient's left eye is looking through the left LCD shutter 134L and the patient's right eye is looking through the right LCD shutter 134R. The infrared LEDs 136 are illuminated to illuminate each eye for tracking eye movement, as described below.

Referring to FIG. 4, a block diagram illustrates the components of the system 102 for measuring visual fixation disparity using the image capture device 100. The system uses a conventional personal computer 140. The computer 140 includes a programmed processor and memory storing programs and data for use during the measurement of visual fixation disparity. The internal components of the computer 140 are well-known and are therefore not described in detail herein. The computer 140 may use any operating system, as necessary or desired, running an application program for the measurement of visual fixation disparity, as described herein.

The computer 140 includes a stereo video card 142 including DVI ports 144 for connection via cables 146 and 148 to an operator LCD monitor 150 and the image capture device 100, respectively. A 3-D synch port 152 is provided for connection via a synch cable 154 to the image capture device 100. A conventional USB port 156 is provided for connection via a USB cable 158 to the image capture device. A keyboard 160 and mouse 162 are connected via respective ports 164 and 166 to the computer 140. The image capture device 100 is also connected via a monitor AC cable 168 and a power supply AC cable 170 to a 120 volt AC source (not shown). A power cable for the computer 140 is not illustrated. Also, the computer 140 may be connected via network cable or wirelessly to other computers or servers, or the like, as necessary or desired.

The implementation of the hardware external to the image capture device 100 and shown in FIG. 4 is by way of example only and is not intended to be limiting. The computer 140 may take any known form, as may the peripheral devices such as the monitor 150, keyboard 160, and mouse 162. Other peripheral devices and memory devices and the like, may also be used.

Figure 5:
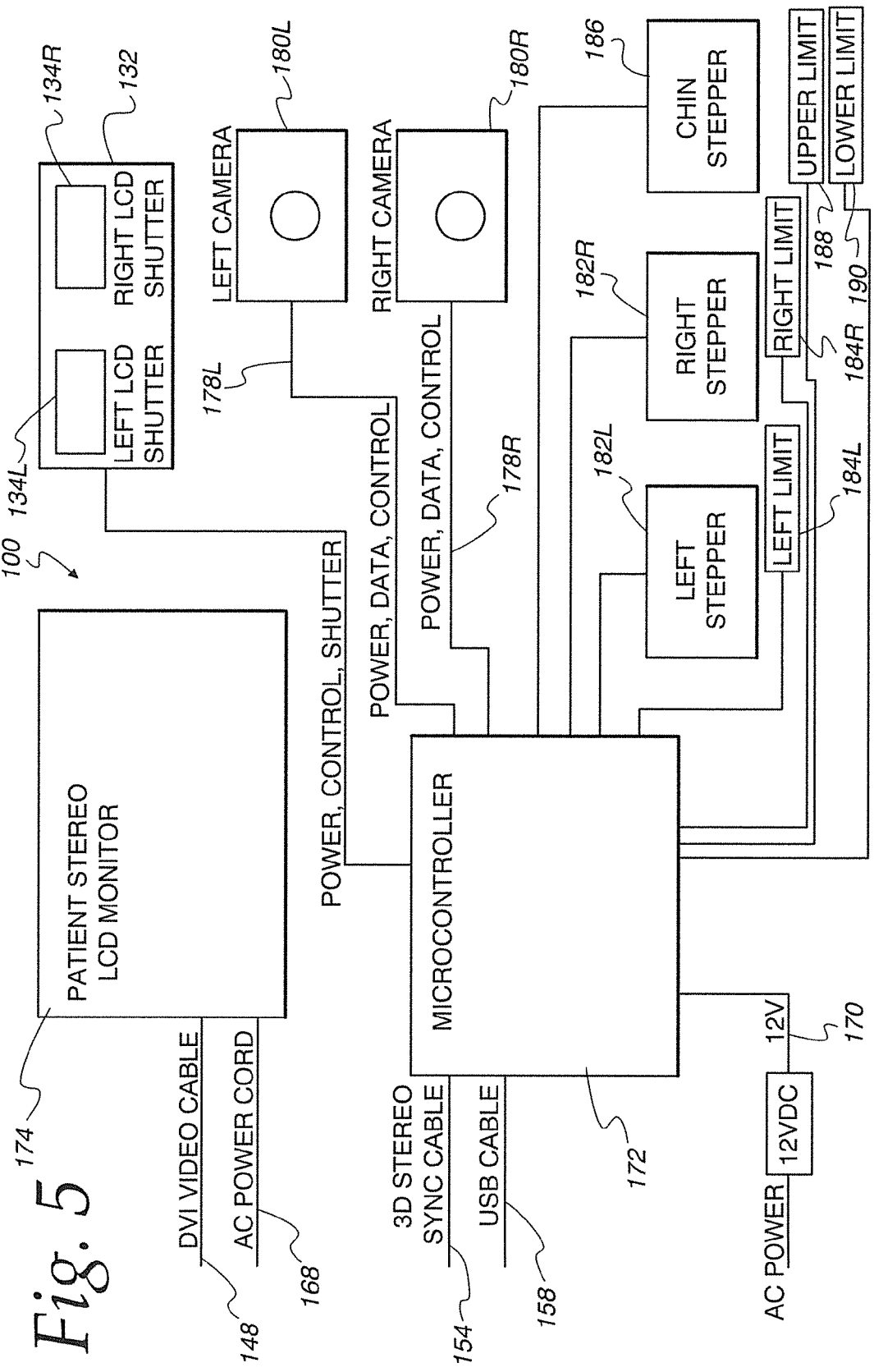
FIG. 5 is a block diagram for the image capture device of FIG. 4.

Referring to FIG. 5, a block diagram illustrates the components in the housing forming the image capture device 100. A microcontroller 172 is connected to the 3-D stereo synch cable 154 and the USB cable 158 as well as the AC power cable 170. The microcontroller 172 comprises a programmed processor and related memory for controlling operation of the image capture device 100 and communicates with the computer 140. As will be apparent, the microcontroller functionality could be implemented in the computer 140, or vice versa. A patient stereo LCD monitor 174 is connected to the DVI video cable 148 and the monitor AC power cord 168. A multi-function electrical cable 176 connects the microcontroller 172 to the circuit board 132 for controlling the left LCD shutter 134L and the right LCD shutter 134R and the LEDs 136. A first camera line 178L connects the microcontroller 172 to a left camera 180L and a right camera line 178R connects the microcontroller 172 to a right camera 180R. The microcontroller 172 is connected to a left stepper motor 182L and a right stepper motor 182R and associated limit switches 184L and 184R. Finally, the microcontroller 172 is connected to a chin stepper motor 186 and an associated upper limit switch 188 and lower limit switch 190. The chin stepper motor 186 controls position of an actuator (not shown) connected through the slot 116 to the chin support 114 for raising and lowering the same.

Figure 6:
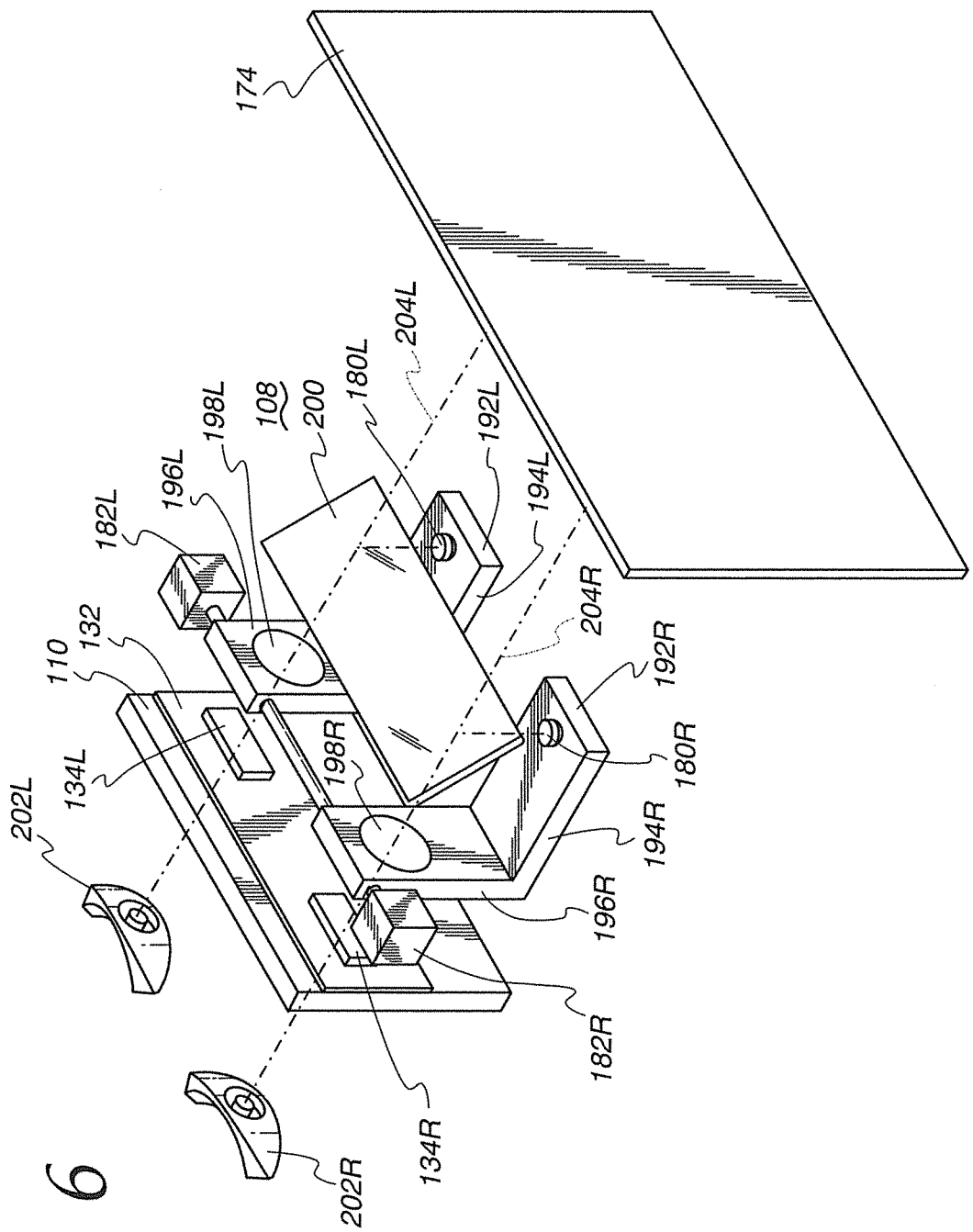
FIG. 6 is a perspective view of the components of the system of FIG. 1 illustrating visual aspects thereof.

FIG. 6 schematically illustrates the functional relationship of the devices in the block diagram of FIG. 5, ignoring the microcontroller 172 and related circuitry, within the housing space 108. Mounting structure for the various components is not shown and does not itself form part of the invention. The stereo LCD monitor 174 is mounted parallel to the front wall 110 a select distance therefrom. A left L bracket 192L and a right L bracket 192R are movably mounted, in any known manner, to the base 104 between the front wall 110 and the patient monitor 174. The left bracket 192L includes a horizontal part 194L supporting the left camera 180L, and an upstanding vertical part 196L supporting a lens 198L. The left bracket 192L is movable from side to side under control of the left stepper 182L. Similarly, the right bracket 192R includes a horizontal part 194R supporting the right camera 180R and an upstanding vertical part 196R supporting a right lens 198R. The right bracket 192R is movable from side to side under control of the right stepper 182R. A splitting mirror 200 is mounted at a 45° angle above the cameras 180L and 180R and between the front plate 110 and the LCD monitor 174. The patient monitor 174 is mounted about one to two feet from the front wall 110. The lenses 198L and 198R have about ½ diopter power so that the images on the patient monitor 174 appear to be about twenty feet from the front wall 110.

With the illustrated hardware, the patient's left eye 202L looks through the left LCD shutter 134L, via a line of sight 204L, and then through the left lens 198L and the splitting mirror 200 to the LCD display 174. Also, the splitting mirror 200 reflects the image from the user's left eye 202L to the camera 180L. The left eye 202L, being illuminated by the infrared LEDs 136 is visible to the left camera 180L. Similarly, the patient's right eye 202R has a line of sight 204R through the right LCD shutter 134R, the right lens 198R, and the splitting mirror 200 which splits the line of sight to the LCD monitor 174 and the right camera 180R. The right eye 202R, being illuminated by the infrared LEDs 136 is visible to the right camera 180R. As such, the eyes 202L and 202R see the display on the LCD monitor 174, while the cameras 180L and 180R and imaging software track movement of the pupils of the eyes 202L and 202R, respectively.

The system 102 measures the proprioceptive disparity, or more generally fixation disparity, between where the eyes are focused at compared to where they automatically want to converge to. The image capture device 100 is used to automatically determine the alignment between the line of sites of the right and left eye. This system will also measure: high frequency tremors, pursuit eye movements, saccadic eye movements, irregular movements, slow drifts, optkinetic reflexes, torsional rotation of the eye and the disparity between our sense of sight and our proprioceptive feedback mechanism. This instrument can measure one eye at a time and/or both eyes at the same time. Its enhanced technology isolates separately the central foveal targets from the peripheral targets and will align the central and peripheral targets together. This system is intended to be used to detect a misalignment between the right and left eye on any human whether they're wearing contacts, glasses or have had surgery in either eye. It may be a self-contained or a portable device either hand held, or table mounted. The device will use a series of targets that simulate optical infinity and/or near targets of various size shape and color.

More particularly, the system 102 is used to measure visual fixation disparity using proprioceptive feedback. This is done by isolating the central vision from the peripheral vision of each eye and using an eye tracking system to capture and monitor the movements of each eye independently. The computer 140 calculates the movements using data from the image capture device 100. This is accomplished using one or more of five different tests. A first test comprises a central monocular test which measures how the central vision of each eye aligns when peripheral vision is not stimulated. The second test is a central peripheral test which measures how eyes are aligned when the peripheral vision and the central vision of each eye are aligned with each other. The third test is an EXO peripheral test which measures how the eyes are aligned when the peripheral vision and the central vision of each eye are uncoupled from each other independently. The fourth test measures torsional rotation of each eye under monocular and binocular conditions. The fifth test measures slow drifts as the patient views targets.

The computer 140 synchronously controls the patient stereo LCD monitor 174 and the LCD shutters 134L and 134R using conventional stereoscopic techniques which are well known. Particularly, the computer 140 uses separate stereo displays for the left and right eyes, each including a distinct image. These displays are alternated in synchronization with the shutters 134L and 134R at 120 frames per second. As is known, the LCD shutters 134L and 134R are controlled to be "opened" in a clear state or "closed" in an opaque state. When the left LCD shutter 134L is open, the image intended for the left eye is displayed on the monitor 174. When the right LCD shutter 134R is open, the image intended for the right eye is displayed on the monitor 174.

Figure 7:
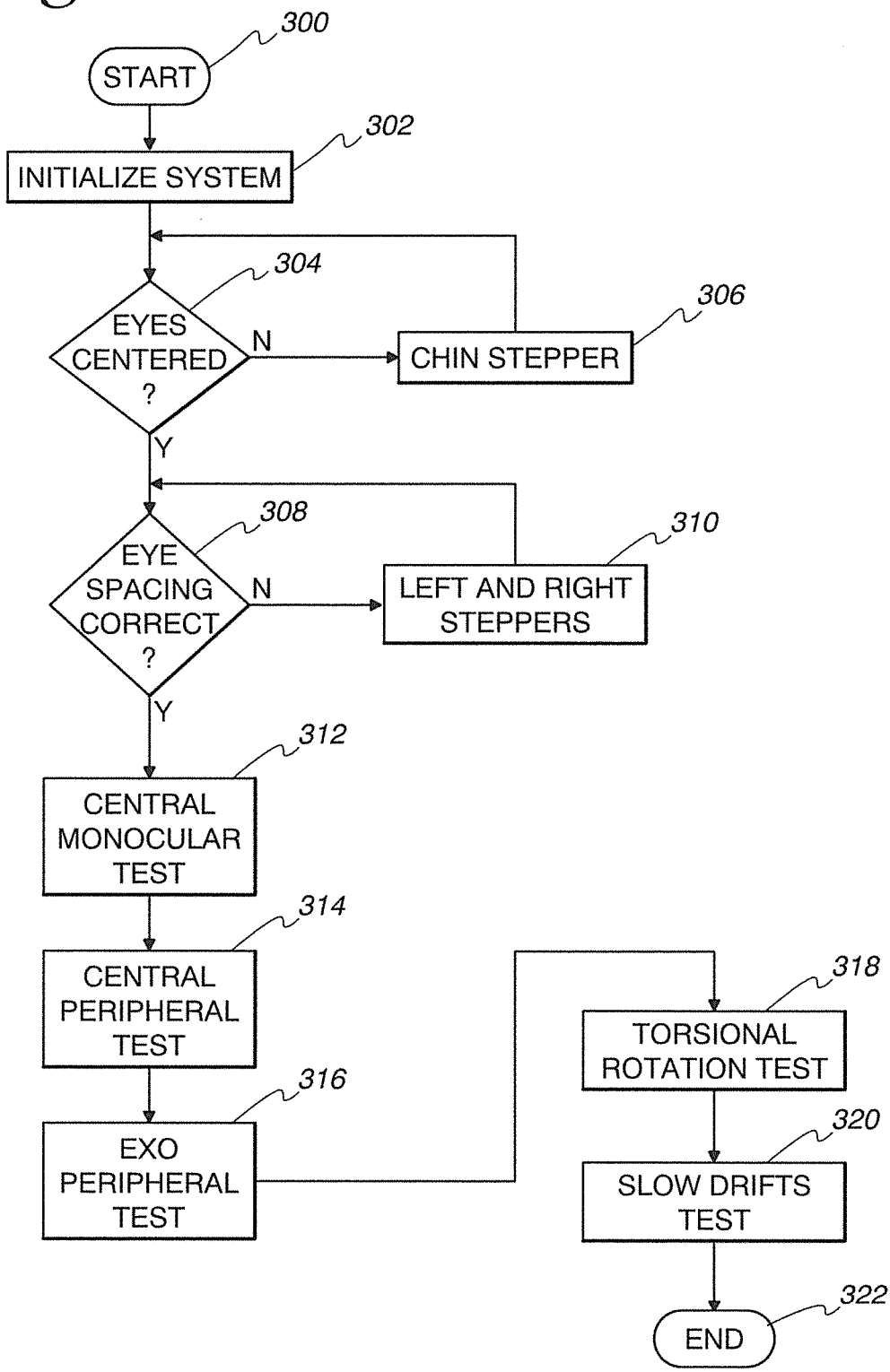
FIG. 7 is a flow diagram illustrating operation of the system of FIG. 1.

Referring to FIG. 7, a flow diagram illustrates operation of the system 102 for measuring fixation disparity using one the five tests discussed above. The system starts at a node 300 and then implements an initialization routine at a block 302. This sets up communication with the microcontroller 172 and initiates operation of the LEDs 136 and the cameras 180L and 180R. Prior to performing the test it is necessary for the patient's eyes to be properly positioned vertically relative to the shutters 134L and 134R and for the cameras 180L and 180R to be aligned with the lines of sight 204L and 204R, respectively. The operator monitor 150 will display the camera images of the patients eyes advantageously relative to a reference grid which can be used by the operator to provide the proper alignment. This is done beginning at a decision block 304 which determines if the eyes are vertically centered. If not, then the chin stepper motor 186 is manually controlled by the operator using any desired input commands at a block 306 to move the chin support 114, see FIG. 2, up or down. The operator will use the operator LCD monitor 150 to view the position of the eyes to determine if they are vertically centered. Once the eyes are vertically centered, then a decision block 308 determines if eye spacing is correct. Eye spacing is correct if the spacing between the lenses 198L and 198R, and thus also camera 180L and 180R, corresponds to the patient's pupillary distance. If not, then the left and right steppers 182L and 182R are manually controlled at a block 310 until the eye spacing is correct. Again, the operator can use the display on the monitor 150 to determine the correct position.

Once the eye spacing is correct, then the operator can implement any one or more of the central monocular tests at a block 312, the central peripheral test at a block 314, the EXO peripheral test at a block 316, the torsional rotation test at a block 318, and the slow drift test at a block 320. Once the operator has completed any or all of the tests, then the operation ends at a node 322.

With the central monocular test, a small central target is viewed and alternated between the left and right eyes in a dark environment while peripheral vision is kept isolated. A small central target is seen only by the left eye for less than one second, then alternated to the right eye for the same amount of time. The movement of each eye is tracked for a period of time as the small central target is alternated between the right and left eyes. The computer 140 relocates the target for both right and left eyes to match the position of each eye in order to measure fixation disparity. Initially, the patient will notice that the target appears to jump from side to side and possibly up and down. Once the tracking system monitors the movement of each eye and relocates the target, then the patient will notice very little movement between the target seen with the right eye and then seen with the left eye. In other words, the two targets appear to be physically coincident.

Figure 8:
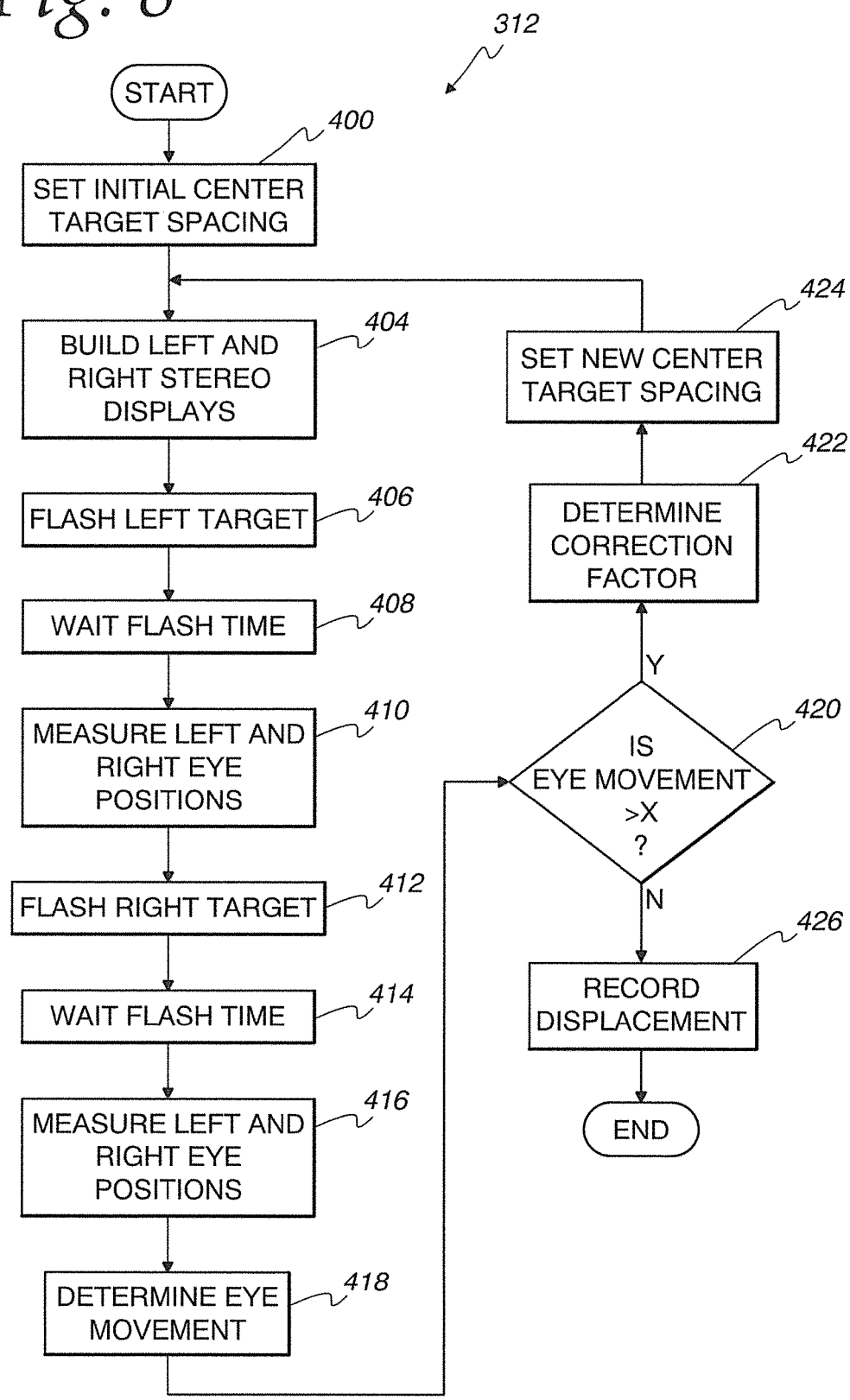
FIG. 8 is a flow diagram illustrating operation of a central monocular test of FIG. 7.
Figure 9A:
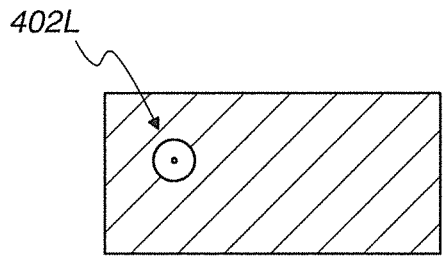
FIGS. 9A and 9B illustrate initial alternating stereo display images with the central monocular test of FIG. 8.
Figure 9B:
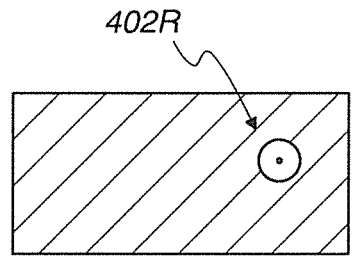

Referring to FIG. 8, a flow diagram illustrates a software routine implemented by the computer 140 for the central monocular test 312. This test begins at a block 400 which sets initial target spacing. The initial center target spacing represents ideal spacing between left and right image targets according to the patient's pupillary distance when viewing an object to focus at infinity. For this test, the LCD monitor 174 displays a black background. The central target comprises a small white circle with a small center dot. As will be appreciated, other target shapes could be used. FIG. 9A illustrates the display image for the left eye, while FIG. 9B illustrates the display image for the right eye. Thus, FIG. 9A illustrates the left eye central target 402L and FIG. 9B illustrates the right eye central target 402R. As is apparent, the locations of the targets 402L and 402R on the display 174 are physically spaced apart based on the initial center target spacing. Once the initial center target spacing is set, then a block 404 builds left and right stereo displays. This comprises building the static displays as shown in FIGS. 9A and 9B respectively, with the positions of the targets 402L and 402R being adjustable under control of the program.

The program then "flashes" the left target 402L at a block 406. This comprises showing the patient the left eye image shown in FIG. 9A. The program waits a select flash time at a block 408. This flash time may be on the order of 0.5 second to 1 second, as necessary or desired. As described above, the stereo control is separately determining which of the left or right eye is viewing this image using a rate on the order of 120 frames per second. At the end of the flash time, then the program measures the left and right eye positions at a block 410. This is done using conventional eye tracking software receiving images from the cameras 180L and 180R. The software determines the pupil position of the patient's left and right eyes. The program then flashes the right target 402R, shown at FIG. 9B, at a block 412. This comprises showing the patient the right eye image shown in FIG. 9B. The program waits the select flash time at a block 414, and measures left and right eye positions at a block 416 at the conclusion of the wait time. The program then determines eye movement at a block 418. This compares the eye positions measured at the blocks 410 and 416. This movement can be side to side and/or up and down. This initially looks at the relative movement of the left and right eyes in order to cancel any head movement and then determines net movement. Based on this, the computer determines a correction factor based on net eye movement which seeks to converge the position of the central targets 402L and 402R so that the patient perceives the left and right targets 402L and 402R to be physically coincident.

Particularly, a decision block 420 determines if the determined eye movement is greater than a select amount X. The amount X is selected to represent no eye movement or that there is substantially no eye movement corresponding to the perceived images being coincident with one another. If the eye movement is greater than X, then the correction factor is determined at a block 422 and new target spacing is set at a block 424 using the correction factor. The program then moves the targets 402L and 402R to the corrected positions and builds the resulting displays at the block 404. The process discussed above continues and is repeated until eye movement is less than X, at which time the total measured displacement, corresponding to the amount the central targets are moved on the monitor 174 and representing fixation disparity, is recorded at a block 426 and the routine ends.

Figure 11:
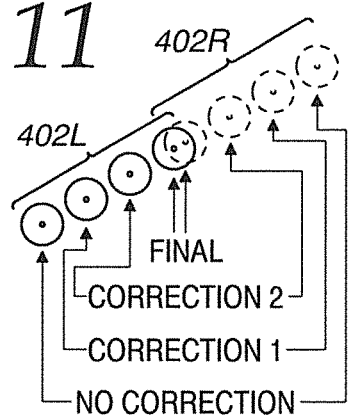
FIG. 11 is a graphic illustrating patient perception during the central monocular test of FIG. 8.
Figure 10A:
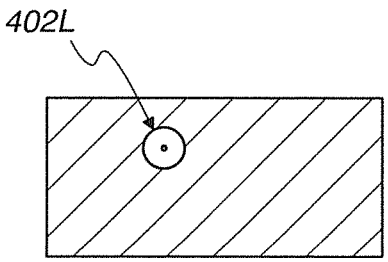
FIGS. 10A and 10B illustrate final alternating stereo display images with the central monocular test of FIG. 8.
Figure 10B:
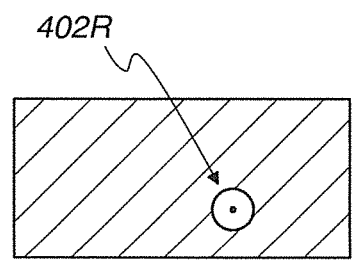

As is apparent, the program may determine that the central target has been moved to the left or to the right or up or down, as necessary to make it appear that the targets 402L and 402R are in the same position. As discussed above, FIGS. 9A and 9B illustrate the initial target spacing. FIGS. 10A and 10B illustrate an example of final target spacing at the conclusion of the test. In this example the left eye central target 402L has been moved up and to the right, while the right eye central target 402R has been moved to the left and down. FIG. 11 successively illustrates the patient's perspective of the targets 402L and 402R from the initial spacing shown as no correction to the final position where the targets are substantially coincident with one another. In this example there are three steps of correction used to move from the initial position to the final correction position. The displacement recorded at the block 426 represents the amount of movement from the no correction position to the final correction position, which can be expressed, for example, in screen pixels or prism diopters, or the like.

The procedure described above which iteratively repositions a central target to measure fixation disparity is also used for the central peripheral test and the EXO peripheral tests. These tests otherwise differ in the use of additional peripheral targets and provide comparative results which illustrate how the peripheral targets affect the measured fixation disparity.

Figure 12:
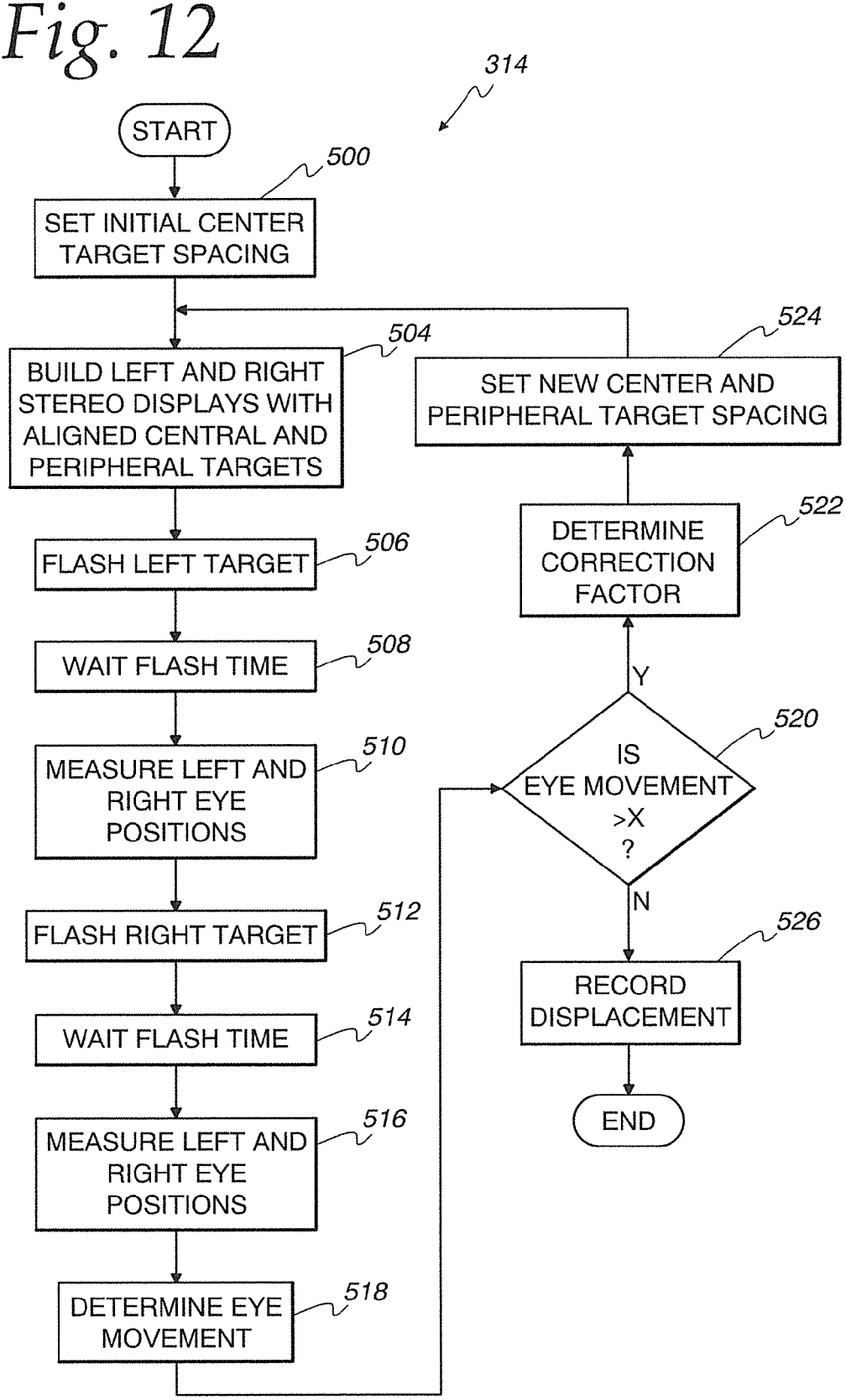
FIG. 12 is a flow diagram illustrating operation of a central peripheral test of FIG. 7.
Figure 13A:
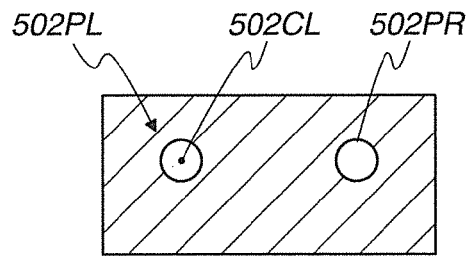
FIGS. 13A and 13B illustrate initial alternating stereo display images with the central peripheral test of FIG. 12.
Figure 13B:
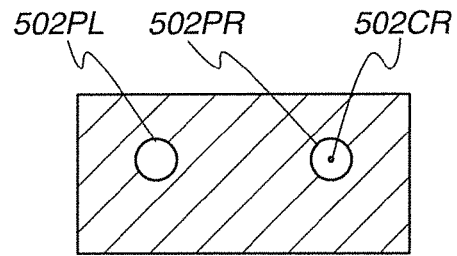

FIG. 12 illustrates a flow diagram for the central peripheral test 314. This flow chart is generally similar to that for the central monocular test 312, see FIG. 8, and the blocks are similarly numbered except being in the 400's rather than the 300's. This routine differs principally in the left and right stereo displays built at a block 504 and adjusted at a block 524. With the central monocular test, the patient's peripheral vision was not stimulated. With the central peripheral test, the small central target is viewed only one eye at a time and alternated between the left and right eyes, while peripheral vision is viewing a constant peripheral target that is geometrically aligned with the central target and thus their central vision. This is illustrated in a basic form in FIGS. 13A and 13B, which shows the left eye display and the right eye display, respectively, corresponding to settings for initial center target spacing, as noted above. For this test, a black background is again used on the display monitor 174. The peripheral target comprises a white circle 502PL and 502PR. The central image target comprises a black dot 502CL and 502CR selectively centered in the corresponding white circles. For this test, the black dot center target is located in the center of the peripheral target which moves with the center target. The left eye display is shown in FIG. 13A in which both peripheral targets 502PL and 502PR are displayed and the left center target 502CL comprises a dot in the center of the left peripheral target 502PL. There is no central target in the right peripheral target 502PR. FIG. 13B illustrates the display for the right eye in which the left eye peripheral target 502PL includes no central target, while the right eye peripheral target 502PR includes the central target 502CR.

As with the central monocular test, the left eye image, as shown in FIG. 13A, is flashed for the wait time and then alternately the right eye image, as shown in FIG. 13B, is flashed for the wait time with eye positions being measured and subsequently eye movement determined at the block 518, as above.

Figure 15:
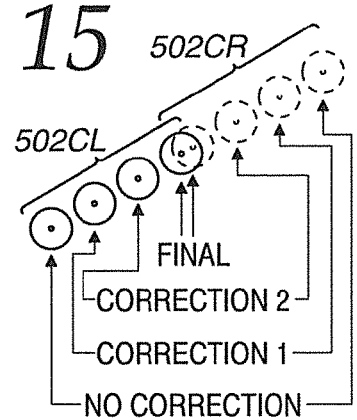
FIG. 15 is a graphic illustrating patient perception during the central peripheral test of FIG. 12.
Figure 14A:
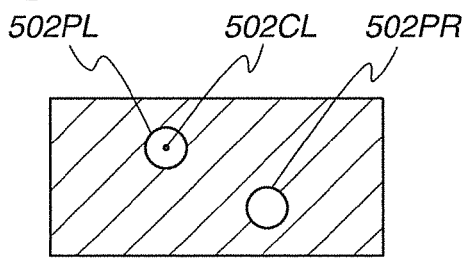
FIGS. 14A and 14B illustrate final alternating stereo display images with the central peripheral test of FIG. 12.
Figure 14B:
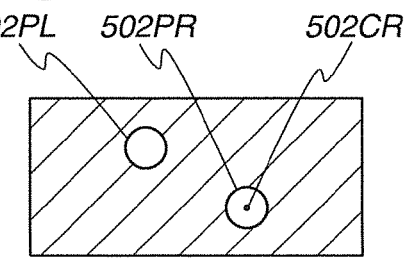

Thus, as described, a small central target 502CL or 502CR is viewed only one eye at a time and alternated between the left and right eyes while the peripheral vision is viewing the constant targets 502PL and 502PR that are geometrically aligned with the central targets 502CL and 502CR. The left central target 502CL is seen for less than one second, then alternated to the right central target 502CR for the same amount of time. The movement of each eye is tracked for a period of time as the target is alternated. The computer 140 relocates the target for both the eyes to match the position of each eye, as discussed above. This is illustrated in FIGS. 14A and 14B, which show the final position. FIG. 15 shows the patient's perception at each step of correction from no correction, based on the image in FIGS. 13A and 13B, to the final correction based on the images shown in FIGS. 14A and 14B. The displacement of the center targets 502CL and 502CR from the position shown in FIGS. 13A and 13B to that shown in FIGS. 14A and 14B, respectively, is recorded at the block 526.

Figure 16:
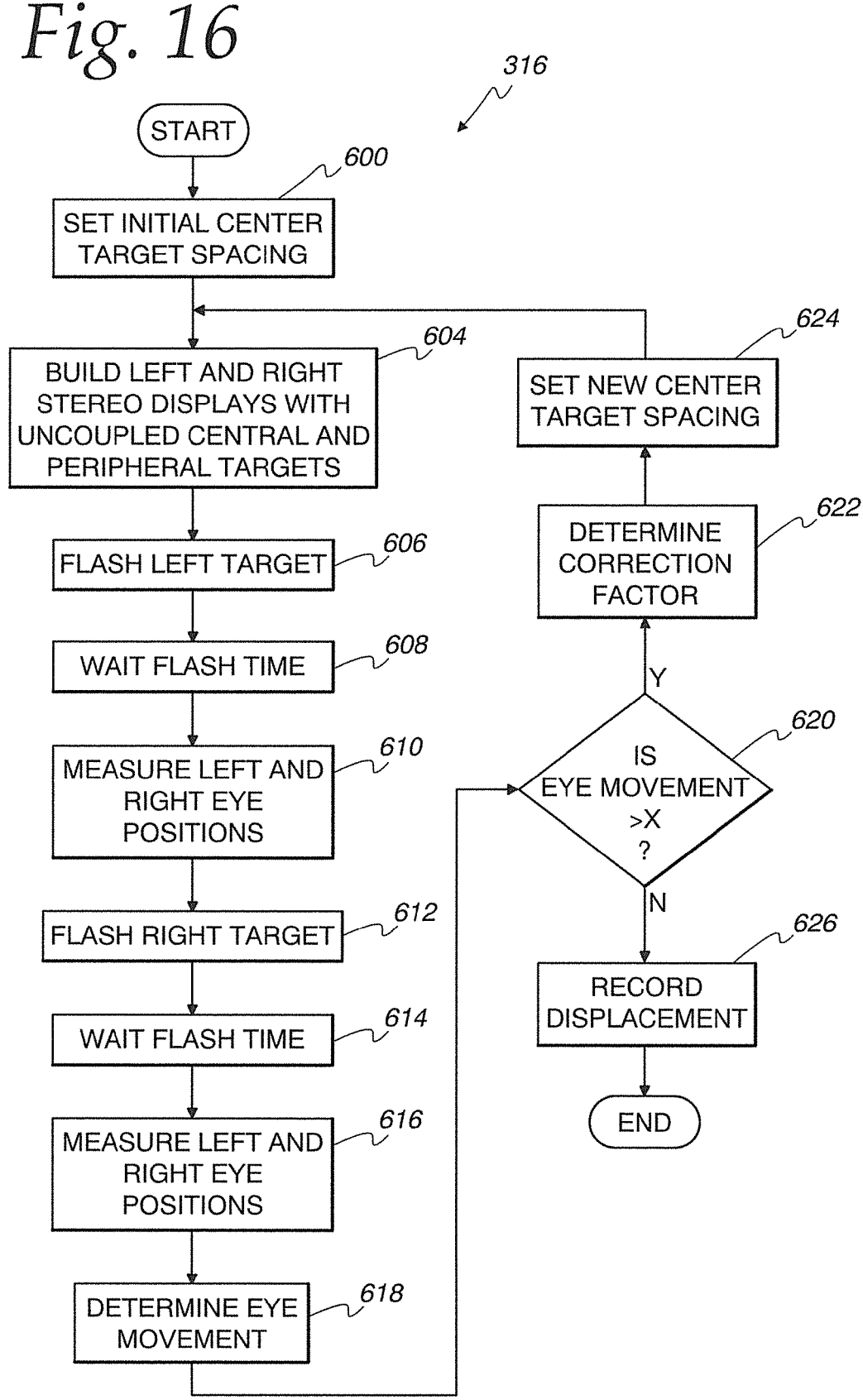
FIG. 16 is a flow diagram illustrating operation of an EXO peripheral test of FIG. 7.

FIG. 16 illustrates a flow diagram for the EXO peripheral test 316. During the EXO peripheral test, peripheral vision is isolated from central vision and adjusted independently until central vision and peripheral vision align with each other. With this test, a small central target is viewed only one eye at a time and alternated between the right and left eyes while peripheral vision is viewing constant peripheral targets that are not geometrically aligned with central vision. These peripheral targets may be stationary, but often are set into motion in order to keep peripheral vision stimulated and fused.

Figure 17A:
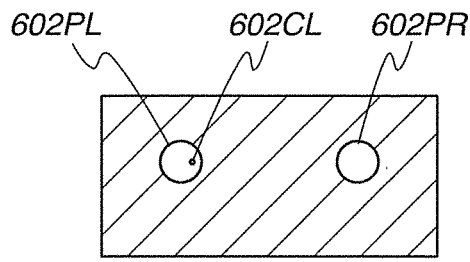
FIGS. 17A and 17B illustrate initial alternating stereo display images with the EXO peripheral test of FIG. 16.
Figure 17B:
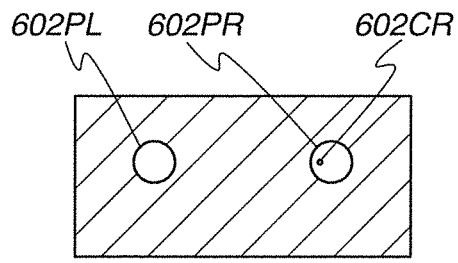
Figure 19:
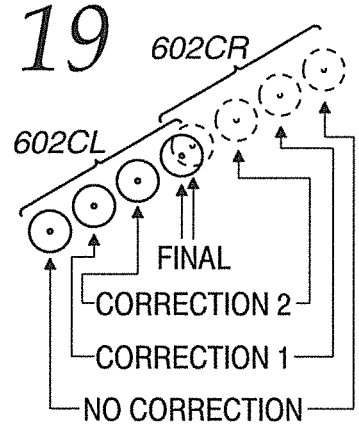
FIG. 19 is a graphic illustrating patient perception during the EXO peripheral test of FIG. 16.
Figure 18A:
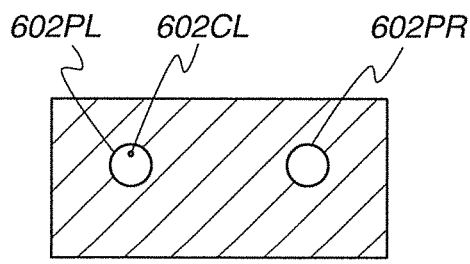
FIGS. 18A and 18B illustrate final alternating stereo display images with the EXO peripheral test of FIG. 16.
Figure 18B:
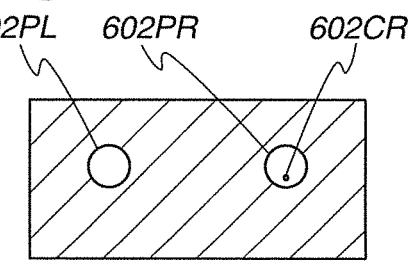

The flow diagram of FIG. 16 is generally similar to the flow charts of FIGS. 6 and 11, and the blocks are similarly numbered except being in the 600 s. This routine differs principally in the left and right stereo displays built at a block 604 and adjusted at a block 624. This is generally illustrated in a basic form in FIGS. 17A and 17B, which illustrate the left eye image displays and right eye image displays, respectively, which are built at the block 604. For this test, a black background is again used on the display monitor 174. The peripheral target comprises a white circle 602PL and 602PR. The central image target comprises a black dot 602CL and 602CR selectively decentered in the corresponding white circles. The two peripheral targets 602PL and 602PR are constant targets but are not geometrically aligned with the central targets 602CL and 602CR. As with the tests above, the central targets 602CL and 602CR are alternately flashed and eye movements measured as discussed between the blocks 606 and 616 to determine movement at a block 618 and, if there is eye movement greater than the amount X at block 620, to determine a correction factor at block 622 and set new center target spacing at a block 624. This proceeds until the center target 602CL and 602CR appear generally coincident with one another using the final correction, as shown in FIG. 19, based on the positions of the display shown in FIGS. 18A and 18B. The displacement of the center targets 602CL and 602CR from the position shown in FIGS. 17A and 17B to that shown in FIGS. 18A and 18B, respectively, is recorded at the block 626.

Thus, with each of the central monocular test, central peripheral test, and EXO peripheral test, a target is presented to the left eye for less than a second, then simultaneously as the target is turned off to the left eye it is turned on to the right eye. This is alternated back and forth as the camera system tracks the movement of the eyes. If the left eye is viewing the target, the right eye goes to a position of rest. This happens for multiple reasons. Initially, this is because there is no target for the right eye to look at, and secondly because the left eye is looking at the target and the patient can't discern which eye they are looking with during the test. The patient often thinks that they are looking at the target with both eyes instead of just one eye. Also, there is no stimulus for the two eyes to work together due to the shutter glass technology.

While the patient is viewing the target with the left eye, the camera system takes a snapshot of the position of the right eye. Then when the target is alternated to the right eye, the right eye will move in order to pick up fixation to the central target. Then another picture of the right eye is taken. The computer 140 calculates where the eye was before the target was presented then where the eye moved to after the target is visible. After alternating between the left and right eyes and taking pictures of both eyes before it sees the target and after it is fixated on the target, the system calculates the movement of each eye and relocates the targets in order to minimize the movement of the eyes as the eye goes from no target to seeing a target. The difference in the peripheral tests is how the peripheral target is presented in relation to the central target. During the central monocular test there is no stimulus to the peripheral vision, since the peripheral vision is looking at a black screen. In the central peripheral test and EXO peripheral test, there is constant stimulus to the peripheral vision of both eyes. The right eye and left eye see separate, constant, and similar targets and the brain puts these independent pictures from each eye together to make a three-dimensional stereoscopic picture. Altering the location of the peripheral images creates more or less three-dimensional depth. Thus, the system allows the patient to have peripheral vision fused together creating a three-dimensional image, while the central vision is isolated from having binocular vision, as only one eye can see one target at a time. This sets up a dynamic way to measure the relationship how our brain fuses a peripheral target in relationship to how it fuses the central target that is being viewed.

Figure 20:
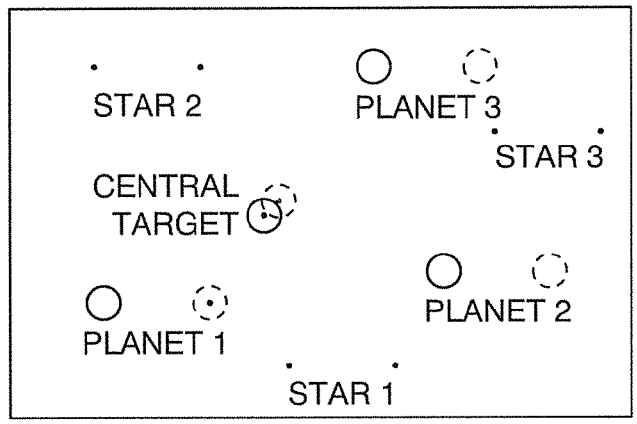
FIG. 20 illustrates an alternative display for peripheral targets with the central peripheral test.
Figure 21:
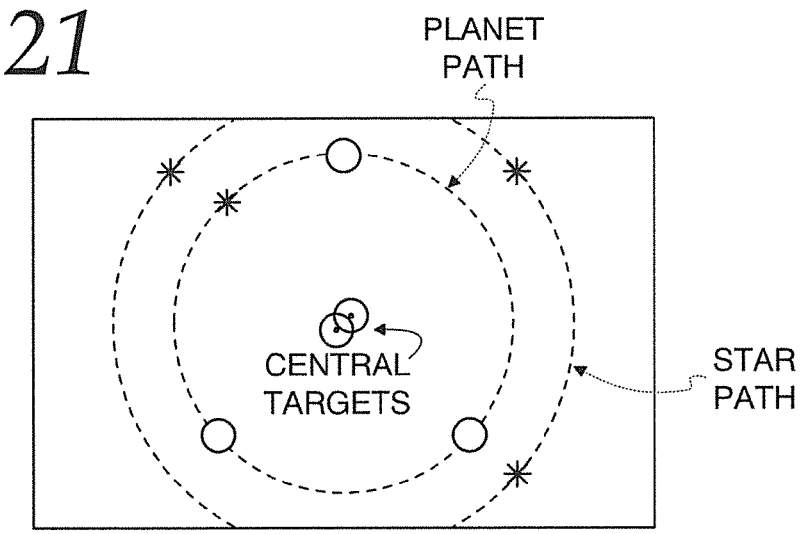
FIG. 21 illustrates the patient's perspective with the peripheral targets of FIG. 20 and illustrating movement of the targets.

As described above, a basic form of the methodology uses a white circle as the peripheral target. Alternative peripheral targets may be used for the central peripheral test and the EXO peripheral test. FIG. 20 illustrates an alternative for the central peripheral test in which a plurality of planets and stars are illustrated as peripheral targets. In this illustration, there are three planets and three stars. With respect to the stereoscopic implementation of the planets, one is shown in solid line, which is for the left eye image, while one is shown in dashed line, which is for the right eye image. Similarly, each star includes two images, one for the left eye and one for the right eye. These stars and planets can be presented in 3-D with shadowing and different colors and the like. Similarly, the planets and stars can be moving as shown in FIG. 21, in which the planets rotate in an orbit around the central targets. Moreover, the planets may spin while going through the orbit. The stars may similarly rotate and spin. As is apparent, additional planets and/or stars could be used, with some planets orbiting in one direction and others in the opposition direction, as with the stars. The rotation of any of these is at the same angular rate, with some in one direction and others in the opposition direction. The planets and the movement are continuous and only the central target flashes. With any option, the peripheral targets are always shown to the left eye and the right eye using the stereoscopic control discussed above, while the central target is alternated or flashed, so that only the left or the right central target is shown at any given time, as discussed above. While the peripheral vision wants to view the peripheral targets, the objective of the test is for the patient to ignore the peripheral targets.

Figure 22:
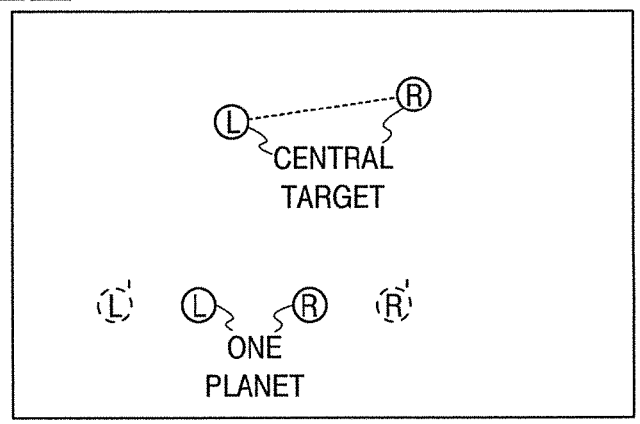
FIG. 22 illustrates an alternative display for the EXO peripheral test.

FIG. 22 illustrates an alternative for the EXO peripheral test in which the peripheral target is a single planet, shown stereoscopically one for the left eye image and one for the right eye image displaced from the central targets and not aligned. In this case, the peripheral targets can be moved left and right, opposite one another, independently of movement of the central target.

With each of the central monocular test, central peripheral test, and EXO peripheral test, the amount of displacement may vary. The recorded displacement data can be used as warranted for preparing prescription lenses to accommodate for the fixation disparity which appropriately adjusts prism or the like for the patient. The target of the test is to determine how the peripheral images impact the central vision perception of the target.

As will be apparent, there are numerous options for how the peripheral targets are displayed, it being understood that for the peripheral tests both the left eye and right eye will always see the left peripheral targets and right peripheral targets, respectively, while the central targets will flash. The invention is not intended to be limited to any form of the peripheral targets or central targets.

With respect to the torsional rotation test, described at the block 318 of FIG. 7, there are six independent muscles that control movement of each eye. Depending on the neurological intervention of each of these muscles, the location of the patient's head in relation to where the patient is looking and the position of the target, above or below, a combination of these muscles are used to move the eyes up, down, left or right. Cranial nerves III and IV and VI work together in order to reposition the eye to different locations. When this happens there is often cyclic rotation of the eye. This rotation can be measured and captured by the computer 140. This is done by noting the rotation of the eyes when the system changes the location of where the eyes are looking. The rotation can be measured in the same fashion as the eye movement is captured. A snapshot, or streaming video of the location of the eye prior to the central target and again after the target is turned off, using the cameras 180L and 180R.

The slow drifts test initiated at the block 320 can also use the camera images. When fixating on a target with our central vision, there is a natural oscillation or very fine eye movement that constantly exists in order to help keep our eyes fixated on the target being viewed. As one stares at a target, the eyes will start to drift away from what is being viewed. These slow drifts can be measured under monocular and binocular conditions. The computer compares images at set intervals using setup parameters with these intervals.

Thus, using the system for measuring visual fixation disparity and the corresponding methodology, the system presents stereoscopic visual content to the patient using central targets and peripheral targets while measuring eye movement to determine fixation disparity.

It will be appreciated by those skilled in the art that there are many possible modifications to be made to the specific forms of the features and components of the disclosed embodiments while keeping within the spirit of the concepts disclosed herein. Accordingly, no limitations to the specific forms of the embodiments disclosed herein should be read into the claims unless expressly recited in the claims. Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A system for measuring visual fixation disparity comprising:
   a display apparatus for presenting stereoscopic visual content to a patient;
   a sensing apparatus for monitoring central vision of the patient;
   a controller for controlling the display apparatus to stereoscopically display a smoothly moving peripheral target with a static central image target to isolate central vision from peripheral vision of the patient and monitor the central vision of the patient.

2. The system for measuring visual fixation disparity of claim 1 wherein the display apparatus comprises a stereo LCD display and synchronously driven LCD shutters.

3. The system for measuring visual fixation disparity of claim 1 wherein the display apparatus comprises a polarized light stereo display and matching polarized eye filters.

4. The system for measuring visual fixation disparity of claim 1 wherein the sensing apparatus comprises left and right image capture devices for tracking pupil position of the patients left and right eyes, respectively.

5. The system for measuring visual fixation disparity of claim 4 wherein the sensing apparatus is selectively adjustable to space the left and right image capture devices corresponding to the patient's pupillary distance.

6. The system for measuring visual fixation disparity of claim 1 wherein the controller controls the display apparatus to stereoscopically display a central image target alternately to a left eye and a right eye of the patient and tracking eye movement for a period of time as the central image target is alternated between the left eye and the right eye, and incrementally relocating the central image target left and right images until the patient perceives the left and right images to be physically coincident.

7. The system for measuring visual fixation disparity of claim 1 wherein the peripheral target and the central image target are stereoscopically consistent with each other.

8. The system for measuring visual fixation disparity of claim 1 wherein the peripheral target and the central image target are intentionally stereoscopically inconsistent with each other.

9. The system for measuring visual fixation disparity of claim 1 wherein the controller controls the display apparatus to stereoscopically display a plurality of smoothly moving peripheral targets with the static central image target.

10. A system for measuring visual fixation disparity comprising:
a display apparatus for presenting stereoscopic visual content to a patient;
a sensing apparatus for tracking eye movement of the patient;
a controller for controlling the display apparatus to stereoscopically display a central image target alternately to a left eye and a right eye of the patient and tracking eye movement for a period of time as the central image target is alternated between the left eye and the right eye, and incrementally relocating the central image target left and right images until the patient perceives the left and right images to be physically coincident.

11. The system for measuring visual fixation disparity of claim 10 wherein the display apparatus comprises a stereo LCD display and synchronously driven LCD shutters.

12. The system for measuring visual fixation disparity of claim 10 wherein the sensing apparatus comprises left and right image capture devices for tracking pupil position of the patients left and right eyes, respectively.

13. The system for measuring visual fixation disparity of claim 12 wherein the sensing apparatus is selectively adjustable to space the left and right image capture devices corresponding to the patient's pupillary distance.

14. The system for measuring visual fixation disparity of claim 10 wherein the controller controls the display apparatus to stereoscopically display a peripheral target stereoscopically consistent with the static central image target to isolate central vision from peripheral vision of the patient and monitor the central vision of the patient.

15. The system for measuring visual fixation disparity of claim 10 wherein the controller controls the display apparatus to stereoscopically display a moving peripheral target stereoscopically consistent with the static central image target to isolate central vision from peripheral vision of the patient and monitor the central vision of the patient.

16. The system for measuring visual fixation disparity of claim 10 wherein the controller controls the display apparatus to stereoscopically display a peripheral target intentionally stereoscopically inconsistent with the static central image target to isolate central vision from peripheral vision of the patient and monitor the central vision of the patient.

17. The system for measuring visual fixation disparity of claim 10 wherein the controller controls the display apparatus to stereoscopically display a moving peripheral target intentionally stereoscopically inconsistent with the static central image target to isolate central vision from peripheral vision of the patient and monitor the central vision of the patient.

18. The system for measuring visual fixation disparity of claim 10 wherein the controller determines eye movement for each eye between a time that the central image target is not visible to each eye and a time that the central image target is visible to each eye.

19. The system for measuring visual fixation disparity of claim 18 wherein the controller relocates the central image target until eye movement is less than a select amount.

20. The system for measuring visual fixation disparity of claim 18 wherein the controller relocates the central image target until there is substantially no eye movement.

21. The system for measuring visual fixation disparity of claim 18 wherein the controller monitors rotation of the eyes when the controller tracks eye movement.

22. The system for measuring visual fixation disparity of claim 18 wherein the controller compares eye tracking images at select intervals to measure slow drifts of the eyes.

* * * * *